US005654141A

United States Patent [19]
Mariani et al.

[11] Patent Number: 5,654,141
[45] Date of Patent: Aug. 5, 1997

[54] AMPLIFICATION BASED DETECTION OF BACTERIAL INFECTION

[75] Inventors: Brian D. Mariani, Philadelphia; Rocky S. Tuan, Chester Springs, both of Pa.

[73] Assignee: Thomas Jefferson University, Philadelphia, Pa.

[21] Appl. No.: 342,091

[22] Filed: Nov. 18, 1994

[51] Int. Cl.$^6$ ................................................ C12Q 1/68
[52] U.S. Cl. ................................... 435/6; 435/91.2
[58] Field of Search ............................... 435/6, 91.2

[56] References Cited

U.S. PATENT DOCUMENTS

| | | | |
|---|---|---|---|
| 4,237,224 | 12/1980 | Cohen et al. | 435/68 |
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,883,750 | 11/1989 | Whiteley et al. | 435/6 |

FOREIGN PATENT DOCUMENTS

| | | | |
|---|---|---|---|
| 329822 | 8/1988 | European Pat. Off. . | |
| 320308 | 12/1988 | European Pat. Off. . | |
| 2 202 328 | 3/1988 | United Kingdom . | |
| WO 8803957 | of 0000 | WIPO | 435/6 |
| 87/00880 | 4/1987 | WIPO . | |
| WO 88/10315 | 6/1988 | WIPO . | |
| WO 89/06700 | 1/1989 | WIPO . | |
| 89/01025 | 3/1989 | WIPO . | |

OTHER PUBLICATIONS

Walker, G. T., et al., Isothermal in vitro amplification of DNA by a restriction enzyme/DNA polymerase system *Proc. Natl. Acad. Sci. (U.S.A.)* 1992, 89:392–396.

Kwoh D., et al., Transcription–based amplification system and detection of amplified human immunodeficiency virus type 1 with a bead–based sandwich hybridization format Proc. Natl. Acad. Sci. (U.S.A.) 1989, 86:1173.

Ohara, O., et al., One-sided polymerase chaim reaction: The amplificaation of cDNA *Proc. Natl. Acad. Sci. (U.S.A.)* 1989, 86:5673–5677.

Wu, D. Y. et al., The Ligation Amplification Reaction (LAR)–Amplification of Specific DNA Sequences Using Sequential Rounds of Template–Dependent Ligation Genomics 1989, 4:560.

Lamballerie et al. A one–step microbil DNA extraction method using "CHelex 100 " suitable for gene amplification *Res. microbiol.* 1992 143–785–790.

Brosius et al. Complete nucleotide sequence of a 16S ribosomal RNA gene from *Escherichia coli Proc. Natl. Acad Sci* 1978 75:4801–4805.

Tompkins L. The Use of Molecular Methods in Infectious Diseases *New England Journal of Medicine* 1992 1290–.

Greisen et al. PCR Primers and Probes for the 16S rRNA Gene of Most Species of Pathogenic Bacteria, Including Bacteria Found in Cerebrospinal Fluid *Jour of Clin Microbio* 1994 32:335–351.

Avaniss–Aghajani et al. Am Molecular Technique for Identification of Bacteria Using Small Subunit Ribosomal RNA Sequences *BioTechniques* 1994 17:144–.

Liebling et al. The Polymerase Chain Reaction for the Detection of Borrelia Burgdorferi in Human Body Fluids *Arthritus and Rheumatism* 1993 36:665–.

Nocton et al. Detection of Borrelia Burgdorferi DNA by Polymerase Chain Reaction in Synovial Fluid From Patients with Lyme Arthritis *New England Jour Med* 1994 330:.

Muralidhar et al. Use of the Polymerase Chain Reaction to Study Arthritis Due to Neisseria Gonorrhoeae Arthritis & Rheumatism 1994 37:71–717.

Kieschi et al. PCR–Based Detection of Mycobacteria in Sputum Samples Using a Simple and Reliable DNA Extraction Protocol Biotechniques 1994 17:844.

Hohlfeld et al. Prenatal Diagnosis of Congential Toxoplasmosis with a Polymerase–Chain Reaction Test on Anmiotic Fluid *New Eng Jour Med* 331:695.

Levine et al. Molecular Genetic Diagnosis of Infected Total Joint Arthroplasty J. Atrhroplasty Dec. 1994, also presented Nov. 18, 1994 Jefferson Orthopaedic Society.

Abbaszadegan et al. Detection of Enteroviruses in Groundwater with the Polymerase Chain Reaction *Applied and Environ. Macrobiol.* 1993 59:1318–1324.

Wilson et al. Amplification of Bacterial 16S Ribosomal DNA with Polymerase Chain Reaction *Journ.of Clin. Microbiol.* 1990 28:1942–1946.

Brakstad et al. Detection of *Staphylococcus Aureus* by Polymerase Chain Reaction Amplication of the Nuc Gene *Journ. of Clin. Microbiol.* 1992 30:1654–1660.

The Stratagene Catalog 1988 Ed. p. 39.

Meier, J. Clin. Microbiology31(3):pp. 646–652 (1993).

*Primary Examiner*—W. Gary Jones
*Assistant Examiner*—Ethan Whisenant
*Attorney, Agent, or Firm*—Woodcock Washburn Kurtz Mackiewicz & Norris

[57] ABSTRACT

A method of detecting a bacterial infection in a patient comprising obtaining a patient sample; obtaining a sample of nucleic acids from the patient sample; separating charged cellular components from the nucleic acids using a mixed bed ion exchange resin; amplifying bacterial nucleic acids in the sample; and detecting the presence or absence of amplified nucleic acids wherein the presence of amplified nucleic acids indicates a bacterial infection.

14 Claims, No Drawings

AMPLIFICATION BASED DETECTION OF BACTERIAL INFECTION

FIELD OF THE INVENTION

The invention is directed to a method of detecting a bacterial infection in a patient using amplification and separation techniques.

BACKGROUND OF THE INVENTION

The accurate diagnosis of infection about orthopaedic implants has long been confounded by the difficulty of retrieval and detection of microorganisms. Diagnostic modalities have included white blood cell counts, erythrocyte sedimentation rates, bone scans, and C-reactive protein. Arthrocentesis with gram stain and culture has typically been the accepted standard for microorganism identification. However, the accuracy of this invasive diagnostic technique is only 80 to 85%. Thus a significant number of joint infections may be underdiagnosed and the clinical decisions, predicated on that information, will be incorrect, if only standard microbiological and serological techniques are employed. In addition, the currently available techniques are labor intensive and costly. All existing techniques suffer from a lack of sensitivity and a high false negative rate.

For situations in which time is of the essence (about 5 hours) such as trauma cases or whenever surgery cannot be planned ahead of time, and where a prosthetic device is being revised, there currently exists no procedure which can provide determinative evidence of infection, or lack thereof, in order for the surgery to properly be performed. For example, if surgery is being performed to revise a previously implanted prosthetic device, and infection was not detected by currently available techniques prior to surgery, surgery may ultimately be delayed due to infectious signs once the incision is made. In certain circumstances, a bone cement block or spacer containing antibiotics may be placed into infected tissue. The present rule of thumb among orthopaedic surgeons requires a waiting period for surgery of six weeks before removing the spacer, due to the inconclusivity of presently available techniques for determining infection. The standard culture technique has a relatively high false negative rate, largely attributed to a periprosthetic glycocalyx, and has been complicated by various antibiotic therapies which often diminish the retrieval of organisms. Furthermore, the subsequent treatment of an infected joint is performed on a purely empirical basis. Testing the efficiency of infectious therapies is largely empirical, since chronic antibiotic therapy renders standard microbiologic tests useless. Sedimentation rates have been unpredictable and may remain elevated for a lifetime, while nuclear radiographic studies are often positive for 18 months even in an uninfected joint.

There is a timely need for a new clinical technique to enhance the diagnostic accuracy of standard radiographic, serologic, and microbiologic techniques for the diagnosis of infection, particularly for infections about a joint implant. Accordingly, a technique is required which can detect the presence or absence of bacterial infection and which may be performed while intraoperative procedures are underway or very soon prior to starting. Where the results of currently available techniques are inconclusive, a procedure is also needed to provide definitive results.

SUMMARY OF THE INVENTION

In accordance with the present invention, a method of detecting a bacterial infection in a patient comprising obtaining a patient sample; obtaining a sample of nucleic acids from the patient sample; amplifying the nucleic acids; and detecting the presence or absence of amplified nucleic acids specific for a bacterial infection wherein the presence of amplified nucleic acids indicates a bacterial infection is provided.

DETAILED DESCRIPTION OF THE INVENTION

The present invention is directed to a method of detecting a bacterial infection in a patient comprising obtaining a patient sample; obtaining a sample of nucleic acids from the patient sample; separating charged cellular contaminants from said bacterial nucleic acids using a mixed bed ion exchange resin; amplifying bacterial nucleic acids present in the sample; and detecting the presence or absence of amplified nucleic acids wherein the presence of amplified nucleic acids indicates a bacterial infection.

The present invention is also useful to differentiate between live and dead bacteria in a patient sample, and to monitor the efficacy of antibiotic treatments during the course of an infection and or treatment of an infection. The methods of the present invention may also be used to detect and discriminate between different bacterial strains and/or species.

The methods of the present invention are directed to a patient suspected of having a bacterial infection. Patients suspected of having bacterial infections include patients with prosthetic devises such as an artificial knee, hip or other joint replacement, patients who have recently had surgery, such as arthroplasty, patients experiencing arthritis, patients experiencing symptoms of bacterial infection, such as inflammation, yet who have not been diagnosed by other techniques as having an infection, patients who may have been exposed to bacteria, and patients who by pre-operative or intra-operative procedures are identified as being suspected of having a bacterial infection.

In accordance with methods of the present invention, methods of detecting bacterial infection in a patient are provided comprising obtaining a patient tissue sample for testing. The tissue sample may be solid or liquid, a body fluid sample such as and not limited to synovial fluid from any body joint such as knee, elbow, hip, digits, ankle, wrist, and shoulder; cartilage, bone, tendon, ligament, intervertebral disc, synovial membrane, saliva, cerebrospinal fluid, sputum, mucus, bone marrow, serum, blood, urine, lymph, tears, or semen, or feces.

Nucleic acids, such as DNA and/or RNA, are obtained from the patient sample. The bacteria detectable by the methods of the present invention include and are not limited to Escherichia, such as E. coli; Streptococcus, such as S. bovis, Streptococci group B; Staphylococcus, such as S. aureus, S. epidermidis; Bacteroides; and the like. Sequences specific to these bacteria which may be detected by the present invention include and are not limited to nucleic acid sequences of bacterial 16S ribosomal RNA (rRNA) genes and sequences conferring antibiotic resistance to bacteria. The 16S ribosomal RNA (rRNA) genes are multi-copied genes which code for rRNA in many bacteria. In addition, sequences which are species specific may be detected by the present invention including and not limited to the ial gene of E. coli, Enterotoxin A gene of Staphylococcus, the non-conserved regions of the 16S rRNA gene of Bacteroides and Streptococcus.

In the use of the present invention in orthopaedic applications, currently known orthopaedically relevant bacterial species possess highly conserved multi-copies of 16S ribosomal genes, which are amenable to hybridization with a single set of oligonucleotide primers for amplification. For PCR-based testing, for example, of orthopaedically relevant specimens, such as synovial fluid, the sample is preferably prepared under conditions that will allow its direct addition to the reaction mixture without adverse effects on the activity of the polymerase enzyme. While a DNA purification step prior to PCR analysis ensures optimal polymerase activity, extremely low bacterial titers present in some synovial fluid aspirates render any purification step impractical if not impossible. Thus, the present invention may include a bacterial lysis and DNA purification for use directly with amplification procedures for use with a patient sample. This allows the rapid and reproducible detection of bacterial infection or bacterial contamination of patient samples.

A synovial fluid sample may be harvested from a patient by inserting a large gauge needle into a joint cavity under sterile conditions. This may be accomplished by directly inserting a needle through the skin into a joint or during surgery after the joint is exposed following incision. A synovial fluid aspirate of about 1 ml to about 2 ml may be obtained by directly inserting a needle through the skin. A synovial fluid sample of up to about 10 ml may be obtained during surgery. Solid samples of synovial membrane, tendon, bone, intervertebral disc, or cartilage may be obtained by biopsy where a sample is excised from the patient.

Synovial fluid is a viscous, complex mixture of macromolecules which complicates routine extraction and/or fractionation of materials contained in the mixture. For example, attempts to pellet infectious bacteria by centrifugation to separate the cells from the fluid are hindered by co-sedimentation of high molecular weight macromolecules. Additionally, some components of the fluid remaining as a result of centrifugation are found to inhibit some amplification techniques, such as PCR.

In the present invention, lysis and release of bacterial DNA using the complete, unprocessed synovial fluid, without bacterial separation overcomes these problems. A mixed-bed ion exchange resin may then be used to effectively remove charged inhibitory components of synovial fluid. A mixed bed ion exchange resin, for purposes of the present invention, is defined as an ion exchange resin having positive and negative charged components such as and not limited to $H^+$ and $OH^-$, which is mixed with a patient sample. The resin absorbs positive and negative charged components of the synovial fluid which inhibit amplification of bacterial DNA. Synovial fluid components include and are not limited to hyaluronic acid, proteoglycans including chondroitin, chondroitin sulfate, and keratin sulfate; mucin, albumin, fat, and mineral salts. The components of synovial fluid are exchanged with or replaced by the components of the resin such that a charged synovial fluid component may be replaced by one or more resin components of the same charge as the synovial fluid component. The resin has a mesh range of about 20 to about 50 which corresponds to a particle diameter of about 300 to about 1180 microns. The present invention includes and is not limited to mixed bed ion exchange resins of BIO-RAD™, such as BIO-RAD™ biotechnology grade mixed bed resin AG 501-X8, 20–50 mesh. The resin is added to a final concentration of about 5% to about 20% (weight/volume) and mixed by vortexing for about one minute. The resin may be removed after use by centrifugation to eliminate components which may inhibit amplification. An aliquot of the DNA contained in the supernatant may then be harvested for amplification.

A small sample from a patient is used in the present invention, for example, about 50 μl to about 100 μl of synovial fluid, mixed with two volumes of a lysis/extraction buffer containing potassium chloride (KCl), Tris-HCl, pH 8.0, ethylene diamine tetraacetate (EDTA), pH 8.0, and a non-ionic detergent such as and not limited to polyoxyethylene sorbitan monolaurate (Tween 20). The final concentrations of each component after dilution are about 50 mM KCl, about 100 mM Tris, about 2 mM EDTA, and about 0.5% Tween 20. The sample is mixed by vortexing followed by heating at 90° C. for 10 minutes. The heat treatment ensures the lysis of the bacterial cell wall and the release of bacterial DNA into solution. The DNA will be protected from degradation at this point by the presence of EDTA. At room temperature, a mixed bed (mixed charge) ion exchange resin (e.g. BIO-RAD™ biotechnology grade mixed bed resin AG 501-X8, 20–50 mesh) is added to a final concentration of about 5% to about 20% (weight/volume), mixed by vortexing, for about one minute. The resin is pelleted by centrifugation.

An adequate aliquot of the supernatant, which contains the extracted DNA, is retrieved and stored at −20° C., or used directly for amplification purposes. Usually a volume of the aliquot, which equals about one to about two tenths of the total amplification volume (about 50 μl to about 100 μl) is added to the amplification. Any primer set may be used that targets a bacteria suspected of causing the infection, such as bacterial 16S ribosomal RNA (rRNA) gene, such as and not limited to the sequences of SEQ ID NO: 1 and SEQ ID NO: 2.

Sequences useful in the amplification methods of the present invention include and are not limited to SEQ ID NO: 1, targeted to the 5' half of the 16S rRNA gene, CGGCAG-GCCTAACACATGCAAGTCG and SEQ ID NO: 2, targeted to the 3' half of the 16S rRNA gene, GGTTGCGGC-CGTACTCCCCAGG. SEQ ID NOS: 1 and 2 are sequences of 16S rRNA gene which are conserved among Escherichia, Streptococcus, Staphylococcus, Bacteroides, and the like. The primers sequences of the present invention were originally isolated from E. coli. Non-conserved sequences of the 16S rRNA gene may also be used in the present invention to identify Escherichia, Streptococcus, Staphylococcus, or Bacteroides. The following sequences may be used in regard to the ial gene of E. coli, the 5' sequence TAATACTCCT-GAACGGCG (SEQ ID NO: 3) and the 3' sequence TTAG-GTGTCGGCTTTTCTG (SEQ ID NO: 4), Enterotoxin A gene of Staphylococcus, including aureus and S. epidermidis, TTGGAAACGGTTAAAACGAA (SEQ ID NO: 5) and GAACCTTCCCATCAAAAACA (SEQ ID NO: 6), the 16S non-conserved region of Bacteroides fragilis, GACGTAAGGGCCGTGCTGATTTGACGTC, (SEQ ID NO: 7) used with universal 16S primer; and various primers that target the non-conserved region of other non-conserved 16S regions depending on species such as species of Streptococcus. In addition, mismatches within the sequences identified above, which achieve the methods of the invention, such that the mismatched sequences are substantially complementary to the bacterial sequence sought to be identified, are also considered within the scope of the disclosure. Mismatches which permit substantial similarity to SEQ ID NOS: 1 and 2, such as and not limited to sequences with similar hydrophobicity and hydrophilicity, will be known to those of skill in the art once armed with the present disclosure. The oligos may also be unmodified or modified.

Nucleic acid extraction and separation are followed by amplification of the same. The amplification step incudes the use of at least one primer sequence which is complementary to a portion of bacterial sequences suspected of infecting the patient.

When an amplification method includes the use of two primers, such as the polymerase chain reaction, one of the two primers of the pair may be SEQ ID NO: 1 or SEQ ID NO: 2, such that one of the primers is specific for the bacterial infection suspected of causing the infection. Alternatively, the two primers may be specific to the bacterial infection, in which case one of the primers may have the sequence of SEQ ID NO: 1 and the second primer may have the sequence of SEQ ID NO: 2.

If it is difficult to determine which bacteria is infecting the patient, or if it is suspected that a variety of bacteria are causing the infection, amplification may be carried out repeatedly with primers specific for different bacterial candidates which are believed to be the cause of the infection.

As used herein, the term "amplification" refers to template-dependent processes and vector-mediated propagation which result in an increase in the concentration of a nucleic acid molecule relative to its initial concentration. As used herein, the term template-dependent process is intended to refer to a process that involves the template-dependent extension of a primer molecule. The term template dependent process refers to nucleic acid synthesis of RNA or DNA wherein the sequence of the newly synthesized strand of nucleic acid is dictated by the well-known rules of complementary base pairing (see, for example, Watson, J. D. et al., In: Molecular Biology of the Gene, 4th Ed., W. A. Benjamin, Inc., Menlo Park, Calif. (1987)). Typically, vector mediated methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., Molecular Cloning (A Laboratory Manual) 1982, Cold Spring Harbor Laboratory, Cold Spring Harbor, N.Y. All references disclosed herein are incorporated by reference in their entirety.

A number of template dependent methods are available to amplify the target sequences present in a sample. One of the best known amplification methods is the polymerase chain reaction (referred to as PCR) which is described in detail in U.S. Pat. Nos. 4,683,195, 4,683,202 and 4,800,159, and Innis et al., PCR Protocols 1990, Academic Press, Inc., San Diego Calif., which are each incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. For certain requirements, a reverse transcriptase PCR amplification procedure may be performed in order to quantify the amount of mRNA amplified. Polymerase chain reaction methodologies are well known in the art.

Another method for amplification is the ligase chain reaction (referred to as LCR), disclosed in EPA No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference in its entirety, describes a method similar to LCR for binding probe pairs to a target sequence.

Qbeta Replicase, described in PCT Application No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio]triphosphates in one strand of a restriction site (Walker, G. T., et al., Proc. Natl. Acad, Sci. (U.S.A.) 1992, 89:392–396, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) involves annealing several probes throughout a region targeted for amplification, followed by a repair reaction in which only two of the four bases are present. The other two bases can be added as biotinylated derivatives for easy detection. A similar approach is used in SDA. Bacterial sequences can also be detected using a cyclic probe reaction (CPR). In CPR, a probe having a 3' and 5' sequences of non-bacterial DNA and middle sequence of bacterial RNA is hybridized to DNA which is present in a sample. Upon hybridization, the reaction is treated with RNaseH, and the products of the probe identified as distinctive products which are released after digestion. The original template is annealed to another cycling probe and the reaction is repeated.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS) (Kwoh D., et al., Proc. Natl. Acad. Sci. (U.S.A.) 1989, 86:1173, Gingeras T. R., et al., PCT Application WO 88/10315, each of which are incorporated herein by reference in its entirety), including nucleic acid sequence based amplification (NASBA) and 3SR. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has bacterial specific sequences. Following polymerization, DNA/RNA hybrids are digested with RNase H while double stranded DNA molecules are heat denatured again. In either case the single stranded DNA is made fully double stranded by addition of second bacterial specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate bacterial specific sequences.

Davey, C., et al., European Patent Application Publication No. 329,822, incorporated by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller, H. I., et al., PCT application WO 89/06700, incorporated by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A., In: PCR Protocols: A Guide to Methods and Applications 1990, Academic Press, N.Y.) and "one-sided PCR" (Ohara, O., et al., Proc. Natl. Acad. Sci. (U.S.A.) 1989, 86:5673–5677), all references herein incorporated by reference in their entirety.

Methods based on ligation of two (or more) oligonucleotides in the presence of nucleic acid having the sequence of the resulting "di-oligonucleotide", thereby amplifying the di-oligonucleotide (Wu, D. Y. et al., Genomics 1989, 4:560, incorporated herein by reference in its entirety), may also be used in the amplification step of the present invention.

Following amplification, the samples may be analyzed by agarose or polyacrylamide gel electrophoresis for rapid and direct visualization of the PCR amplification products. When applicable, gels are stained with a DNA-binding fluorescent dye, such as ethidium bromide, to visualize bacterial DNA specific amplified products. Additionally, to increase the sensitivity of detection of amplified bacterial products, DNA hybridization techniques using DNA/RNA probes complementary to the 16S ribosomal RNA gene, for example, may be used to analyze the reaction products which are fixed, or blotted, onto membrane filters. The reaction products may be fixed either directly (dot/slot blots) or after transfer from the electrophoretic gel (Southern blot). Hybridization analysis allows detection of amplified products not visualized by fluorescent dye staining, and the qualitative discrimination between bacterial amplified products and any background products generated from human DNA resulting from nonspecific annealing of the oligonucleotide primers. The selective use of DNA hybridization thus provides high specificity as well as enhanced sensitivity. Unequivocal identification of bacterial genotypes is achieved by means of restriction endonuclease-based sequence polymorphism of the amplified DNA products as analyzed by Southern blotting. The sequence conservation among these species, permits detection of sequences, such as sequences of the 16S rRNA gene, which are shared by bacteria. There are also species-specific sequence polymorphisms between them that allow for species discrimination by the use of restriction endonucleases that recognize these sequence differences. An enzyme digestion step using appropriate restriction endonucleases may be preformed prior to analysis by gel electrophoresis which permits genotypic identification of bacterial species on the basis of restriction fragment length polymorphism (RFLP) patterns generated from a clinical sample, by comparison to patterns generated from known controls. Controls may be used to confirm the amplification product. For example, a marker lane may be included in the electrophoresis gel which may be hybridized with a probe during Southern hybridization thus providing the amplified product size. Similarly, in a dot-blot or slot-blot, at least one well may be hybridized with a probe to identify the amplified product.

The 16S gene which codes for 16S ribosomal RNA, generated from purified *E. coli* DNA and labeled by standard radioactive or non-radioactive labeling procedures, may be used as a hybridization probe and may range in length from about 200 base pairs to about 1000 base pairs, preferably about 900 base pairs. Alternatively, the probe may be an oligo of a length of about 10 to about 30 nucleotides, preferably about 20, 22, or 25 nucleotides. These probing strategies greatly increase the sensitivity of detection and the identification of amplified products present at concentrations too low for direct visualization in the gels with fluorescent DNA stains. An added advantage of hybridization analysis, which may be carried out at high stringency conditions, is the ability of the 16S rRNA gene-specific probe to discriminate against non-bacterial amplified product non-specifically amplified from contaminating human DNA. This aspect of the invention provides extreme specificity for the detection of bacterial infection in patient samples.

Alternatively, gel electrophoresis may be omitted and the amplified products blotted directly onto nitrocellulose or nylon membranes using a standard slot-blot or dot-blot apparatus. This allows direct hybridization analysis of the sample without added manipulation of the DNA, and circumvents its potential loss in the electrophoretic step and the non-uniformity of transfer from the gel. Such slot-blots or dot-blots are processed for hybridization analysis using the same probing strategies as described above. This option would be considered when direct visualization of the PCR products is not required.

The present invention illustrates the use of the molecular biology techniques, polymerase chain reaction (PCR) for example, to amplify the bacterial DNA retrieved from an infected joint. The amplified DNA may be visualized by agarose gel electrophoresis and Southern hybridization with a radioactive probe such as $^{32}P$, biotin, digoxygenin, or fluorescent stains such as ethidium bromide, to confirm the presence or absence of bacteria. Species-specific identification of bacteria, and differentiation between live and dead bacteria, are also within the scope of the present invention.

A diagnostic kit for detecting bacterial infections comprising at least one primer which is complementary to a bacterial sequence and a means for visualizing amplified DNA is also within the scope of the present invention. Alternatively, the kit may comprise two primers. In either case, the primers may be selected from the group consisting of SEQ ID NOS: 1 and 2, for example. The diagnostic kit of the present invention may comprise one or more of a fluorescent dye such as ethidium bromide stain, $^{32}P$, digoxygenin, and biotin, as a means for visualizing amplified DNA. Optionally the kit may include a mixed bed ion exchange resin, size markers, positive and negative controls, and/or a probe specific to the amplified product.

The following example is illustrative but is not meant to be limiting of the invention.

EXAMPLE 1

The sensitivity of the method of the present invention was determined as follows. Known concentrations of orthopaedically relevant bacterial species E. coli were inoculated into sterile synovial fluid. Separate preparations of E. coli in synovial fluid were prepared in serial dilution series using a ten fold dilution factor for each sample with concentrations ranging from $1 \times 10^6$ cells/100 µl of synovial fluid sample to one cell/100 µl. The dilution series was repeated separately for each of the following bacteria Streptococcus bovis, Streptococci group B, Staphylococcus aureus and Staphylococcus epidermidis, and Bacteroides. The bacterial inoculum was prepared using sterile saline solution and adding synovial fluid in a 10 µl volume. Two volumes of lysis/extraction buffer was added to each sample and processed as described above. Using agarose gel electrophoresis and ethidium bromide staining for DNA product visualization, PCR product was reproducibly detected from a sample originally containing $1 \times 10^3$ bacteria/100 µl of sample or greater for all species tested using the primers of SEQ ID NO: 1 and SEQ ID NO: 2.

The thermocycling conditions were as follows: denaturation at 94° C. for 1 minute, annealing at 55° C. for 1 minute and extension at 72° C. for 2 minutes. PCR reactions were carried out for 30–35 cycles. A precycle denaturation step at 94° C. for 5 minutes may be included. PCR amplification was performed using a commercially packaged kit by Perkin-Elmer GeneAmp PCR Reagent Kit, according to the manufacturer's specifications. Amplification products were analyzed by agarose or polyacrylamide gel electrophoresis.

For these tests, about 300 µl of the starting lysis/extraction sample was tested, and only about 10 µl was added to the 100 µl volume of PCR reaction. Of that volume, typically one fifth was analyzed by gel electrophoresis. Thus, on average 1/150 of the sample was actually used for the final analysis. Using such minimal sample size for the PCR procedure and the subsequent Southern blot hybridization bacterial PCR products from samples containing 1 to 10 cells per synovial fluid specimen are detected.

EXAMPLE 2

RL is a 72 year old male with a long history of degenerative arthritis of both knees, unresponsive to conservative management. He was in excellent general medical health, and took no medication other than non-steroidal anti-inflammatory drugs. His physical examination revealed a healthy male, 5'10" and weighing 195 lbs., with 5° varus deformities of both knees which were partially passively correctable. Knee motion was seen from 5° to 125° bilaterally with reproduction of the pain throughout the range of motion. There was no effusion or synovitis or evidence of inflammatory problem. He had no injections or prior surgical procedures.

Bilateral total knee arthroplasties were performed using a posterior cruciate substituting system. The patient had a completely benign perioperative course and received 48 hours of postoperative intravenous antibiotics in addition to his preoperative intravenous bolus. His first postoperative assessment at six weeks showed bilateral range of motion from 5° to 110° with good stability, no pain, and no evidence of inflammation. Radiographs showed satisfactory fixation and alignment of the prosthetic components.

The patient remained in good health until 11 months after surgery when, without traumatic provocation or known infectious exposure, he noticed swelling, warmth, and erythema about the right knee. He became systemically ill and was admitted to the hospital in a febrile condition. Urine and blood cultures taken on admission were negative. Chest X-ray showed no evidence of infection. The patient's white blood cell count was 9.9 with 66 segs and 17 bands. The erythrocyte sedimentation rate, ESR, was 61. Joint aspiration in the office produced a gram stain that was negative and a culture that grew group B streptococcus from the broth only after 5 days. Following admission and aspiration, the patient received two days of cefazolin followed by two days of ceftriaxone. He was not responsive to conservative treatment, and antibiotic therapy was unsuccessful in eradicating the infection. The patient was brought to surgery four days after admission and approximately seven days after the first signs of knee inflammation.

Intraoperative evaluation was remarkable for thin watery infected joint fluid, a flagrant synovitis, and stigmata consistent with infection. The components were not loose, but were removed and an antibiotic spacer block impregnated with Tobramycin implanted. Joint fluid aspirated at the time of surgery was negative for infection by gram stain and standard culture techniques.

Fluid aspirated from the joint at the time of surgery was processed for PCR using primers specific for DNA of bacterial 16S ribosomal gene. Synovial fluid sample was diluted in a lysis/extraction buffer, mixed and heated to achieve bacterial cell lysis. At room temperature, mixed bed (mixed charge) ion exchange resin was added to a final concentration of 10% (wt/vol), mixed and centrifuged. An aliquot of supernatant was removed for PCR analysis using the primer sequences of SEQ ID NOS: 1 and 2. The thermocycling conditions were as follows: denaturation at 94° C. for 1 minute, annealing at 55° C. for 1 minute and extension at 72° C. for 2 minutes. PCR reactions were carried out for 30–35 cycles. A precycle denaturation step at 94° C. for 5 minutes may be included. PCR amplification was performed using a commercially packaged kit by Perkin-Elmer GeneAmp PCR Reagent Kit, according to the manufacturer's specifications.

The amplified DNA sample was analyzed by gel electrophoresis and the presence of bacterial genes ascertained by Southern blotting and radioactive probing, thus confirming the presence of bacteria within the knee despite the negative intraoperative microbiologic studies.

The preoperative gram stain showed no organisms, and the culture only became positive in the broth after five days. Despite a dramatic unmistakable clinical appearance for infection, intraoperative cultures failed to show any growth at five days and the intraoperative gram stain was also negative. On the other hand, molecular amplification by PCR showed positive results and even in the initial phase of analysis, yielded an answer within four to six hours. This case report illustrates the power of the PCR technique in conjunction with DNA hybridization for the detection of bacteria in synovial fluid about an arthroplasty. The application of molecular amplification techniques significantly changes existing algorithms for the diagnosis of infected joint arthroplasties and radically enhances the efficiency of the treatments.

Various modifications of the invention in addition to those shown and described herein will be apparent to those skilled in the art from the foregoing description. Such modifications are also intended to fall within the scope of the appended claims.

What is claimed is:

1. A method of detecting a bacterial infection in a patient comprising:
obtaining a patient sample;
obtaining a sample of nucleic acids from said patient sample;
separating charged cellular contaminants from said nucleic acids with a mixed bed ion exchange resin;
amplifying by the polymerase chain reaction a bacterial nucleic acid sequence suspected of being associated with thereby producing amplified nucleic acids; and
detecting the presence or absence of said amplified nucleic acids wherein the presence of amplified nucleic acids indicates a bacterial infection.

2. The method of claim 1 wherein said patient sample is selected from the group consisting of synovial fluid, cartilage, bone, tendon, ligament, intervertebral disc, synovial membrane, saliva, cerebrospinal fluid, sputum, mucus, bone marrow, serum, blood, urine, lymph, tears, semen, and feces.

3. The method of claim 1 wherein said bacterial infection is selected from the group consisting of Streptococcus, Staphylococcus, and Bacteroides.

4. The method claim 1 wherein amplifyig bacertial nucleic acids comprises using at least one primer selected from the group consisting of SEQ ID NO: 1 and SEQ ID NO: 2.

5. The method of claim 1 wherein amplifying bacterial nucleic acids may be performed by an amplification method selected from the group consisting of polymerase chain reaction, ligase chain reaction, repair chain reaction, cyclic probe reaction, nucleic acid sequence based amplification, strand displacement amplification, and Qβ replicase.

6. The method of claim 1 wherein amplifying bacterial nucleic acids is performed by the polymerase chain reaction.

7. A method of detecting a bacterial infection in a patient comprising:
obtaining a patient sample;
obtaining a sample of nucleic acids from said patient sample;
separating charged cellular contaminants from said nucleic acids with a mixed bed ion exchange resin;
amplifying by the polymerase chain reaction bacterial nucleic acids present in a patient sample thereby producing amplified nucleic acids wherein said polymerase chain reaction comprises at least one primer selected from the group consisting of SEQ ID NO: 1 and SEQ ID NO: 2; and
detecting the presence or absence of said amplified nucleic acids wherein the presence of amplified nucleic acids indicates a bacterial infection.

8. A method of detecting a bacterial infection in a patient comprising:
obtaining a patient sample;
obtaining a sample of nucleic acids from said patient sample;
separating charged cellular contaminants from said nucleic acids with a mixed bed ion exchange resin;
amplifying by the polymerase chain reaction bacterial nucleic acids present in a patient sample thereby producing amplified nucleic acids wherein said polymerase chain reaction comprises the use of two primers, a first primer comprising the sequence of SEQ ID NO: 1 and a second primer comprising the sequence of SEQ ID NO: 2.

9. A diagnostic kit for the detection of a bacterial infection in synovial fluid comprising a mixed bed ion exchange resin, at least one primer selected from the group consisting of SEQ ID NO: 1 and SEQ ID 2, and extraction buffer; said kit useful for detecting a bacterial infection.

10. A method of detecting a bacterial infection in a patient comprising:
obtaining a synovial fluid sample from a patient suspected of having a bacterial infection;

obtaining a sample of nucleic acids from said patient sample;

separating charged cellular contaminants from said nucleic acids with a mixed bed ion exchange resin;

amplifying bacterial nucleic acids suspected of being associated with said bacterial infection present in said patient sample thereby producing amplified nucleic acids; and detecting the presence or absence of said amplified nucleic acids wherein the presence of amplified nucleic acids indicates a bacterial infection.

11. A method of detecting a bacterial infection in a patient comprising:

obtaining a patient sample;

obtaining a sample of nucleic acids from said patient sample;

separating charged cellular contaminants from said nucleic acids with a mixed bed ion exchange resin;

amplifying bacterial nucleic acids specific for 16S rRNA, ial gene sequences, or Enterotoxin A sequences present in a patient sample thereby producing amplified nucleic acids; and detecting the presence or absence of said amplified nucleic acids wherein the presence of amplified nucleic acids indicates a bacterial infection.

12. A method of detecting a bacterial infection in a patient comprising:

obtaining a synovial fluid sample from a patient suspected of having a bacterial infection;

obtaining a sample of nucleic acids from said patient sample;

separating charged cellular contaminants from said nucleic acids with a mixed bed ion exchange resin;

amplifying a bacterial nucleic acid sequence within a sequence selected from the group consisting of 16S rRNA, ial or Enterotoxin A present in said sample thereby producing amplified nucleic acids; and detecting the presence or absence of said amplified nucleic acids wherein the presence of amplified nucleic acids indicates a bacterial infection.

13. A method of detecting a bacterial infection in a patient comprising:

obtaining a synovial fluid sample from a patient suspected of having a bacterial infection;

obtaining a sample of nucleic acids from said patient sample;

separating charged cellular contaminants from said nucleic acids with a mixed bed ion exchange resin;

amplifying a bacterial nucleic acid sequence within a sequence suspected of being associated with said bacterial infection present in said sample thereby producing amplified nucleic acids; and detecting the presence or absence of said amplified nucleic acids wherein the presence of amplified nucleic acids indicates a bacterial infection.

14. A diagnostic kit for the detection of a bacterial infection in synovial fluid comprising a mixed bed ion exchange resin, at least one primer complementary to a bacterial sequence suspected of infecting synovial fluid, and extraction buffer; said kit useful for detecting a bacterial infection.

* * * * *

UNITED STATES PATENT AND TRADEMARK OFFICE
CERTIFICATE OF CORRECTION

PATENT NO. : 5,654,141

DATED : August 5, 1997

INVENTOR(S) : Mariani et al.

It is certified that error appears in the above-indentified patent and that said Letters Patent is hereby corrected as shown below:

Title page, column 2, line 7 delete "Am Molecular" and insert -- A Molecular -- therefor.

At Column 13, line 41, after "with" and before "thereby" insert -- said bacterial infection present in said patient sample --

At Column 13, line 54, delete "amplifying bacertial" and insert -- amplifying bacterial -- therefor.

Signed and Sealed this

Twenty-fifth Day of November, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 1:

```
CGGCAGGCCT AACACATGCA AGTCG                    25
```

( 2 ) INFORMATION FOR SEQ ID NO: 2:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 2:

```
GGTTGCGGCC GTACTCCCCA GG                       22
```

( 2 ) INFORMATION FOR SEQ ID NO: 3:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 3:

```
TAATACTCCT GAACGGCG                            18
```

( 2 ) INFORMATION FOR SEQ ID NO: 4:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 4:

```
TTAGGTGTCG GCTTTTCTG                           19
```

( 2 ) INFORMATION FOR SEQ ID NO: 5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear (  i  i  ) MOLECULE TYPE: DNA (  x  i  ) SEQUENCE DESCRIPTION: SEQ ID NO: 5:
TTGGAAACGG TTAAAACGAA                    20

( 2 ) INFORMATION FOR SEQ ID NO: 6:

(  i  ) SEQUENCE CHARACTERISTICS:
( A ) LENGTH: 20
( B ) TYPE: nucleic acid
( C ) STRANDEDNESS: single
( D ) TOPOLOGY: linear (  i  i  ) MOLECULE TYPE: DNA (  x  i  ) SEQUENCE DESCRIPTION: SEQ ID NO: 6:
GAACCTTCCC ATCAAAAACA                    20

( 2 ) INFORMATION FOR SEQ ID NO: 7:

(  i  ) SEQUENCE CHARACTERISTICS:
( A ) LENGTH: 28
( B ) TYPE: nucleic acid
( C ) STRANDEDNESS: single
( D ) TOPOLOGY: linear (  i  i  ) MOLECULE TYPE: DNA (  x  i  ) SEQUENCE DESCRIPTION: SEQ ID NO: 7:
GACGTAAGGG CCGTGCTGAT TTGACGTC           28